United States Patent [19]

Henry

[11] 4,452,886
[45] Jun. 5, 1984

[54] NOVEL PHOTON ABSORBING OR EMITTING POLYMERS AND THEIR USE AS REAGENTS IN IMMUNOASSAY SYSTEMS

[76] Inventor: Robert P. Henry, 15 Longjumeau St., Ballainvilliers 91160, France

[21] Appl. No.: 303,995

[22] Filed: Sep. 21, 1981

[51] Int. Cl.³ .................... G01N 33/54; C12N 9/96
[52] U.S. Cl. ............................ 435/7; 435/188;
435/810; 436/544; 436/546; 260/112 R; 260/121
[58] Field of Search .............. 435/4, 7, 188, 810; 436/544, 546; 260/112 B, 121; 424/3

[56] References Cited

U.S. PATENT DOCUMENTS

| | | | |
|---|---|---|---|
| 3,312,599 | 4/1967 | Koshland et al. | 435/188 |
| 3,791,932 | 2/1974 | Schuurs et al. | 435/7 |
| 4,046,871 | 9/1977 | Reckel | 260/121 |
| 4,166,105 | 8/1979 | Hirschfeld | 424/3 |
| 4,169,137 | 9/1979 | Hirschfeld et al. | 424/3 |
| 4,201,857 | 5/1980 | Krasnobajew et al. | 435/188 |
| 4,261,968 | 4/1981 | Ullman et al. | 435/7 |
| 4,287,300 | 9/1981 | Gibbons et al. | 435/7 |
| 4,302,536 | 11/1981 | Longenecker | 435/7 |

OTHER PUBLICATIONS

Baumann, "Plastics and Plastic Foams", *Chemical Abstracts*, vol. 93, No. 10 (1980), p. 34, Absts. No. 96117n.
Carraher et al., "Organotitanium Polydyes Derived from Phenylsulfon-phthalein Dyes, and Congo Red, Eriochrome, Black T, Nigrosine and Indigo".
Carmine–Synthesis and Doping Characteristics, *J. Macromol. Sci.-Chem.*, vol. A15, No. 5, (1981) pp. 773–785.

*Primary Examiner*—Esther M. Kepplinger
*Attorney, Agent, or Firm*—Allen R. Kipnes

[57] ABSTRACT

New polymers are disclosed which absorb or emit photons in the visible or ultraviolet spectrum. The polymers when bound to ligands or receptors are useful as reagents for the detection of substances in physiological fluids. Also disclosed are methods of preparing said polymers and reagents and methods of employing said reagents in immunoassay systems.

57 Claims, No Drawings

NOVEL PHOTON ABSORBING OR EMITTING POLYMERS AND THEIR USE AS REAGENTS IN IMMUNOASSAY SYSTEMS

BACKGROUND OF THE INVENTION

The present invention relates to new polymers as reagents for the qualitative and quantitative measurement of ligands and receptors in physiological fluids.

In the past several years much attention has focused on the need to provide economical and rapid means of detecting the presence or absence of biologically active substances in physiological fluids. For example, the treatment of various diseases with drugs having a narrow therapeutic dosage range requires a safe and effective means for accurately determining the amount of drug in the body so that a proper dosage schedule may be tailored to the individual patient.

Further, there is a growing need for an immunoassay system which can be performed by a patient at home. Such a system may be used for example to monitor drug levels, detect vitamin deficiencies, and as a reliable test for pregnancy and fertility.

There presently exist several immunochemical methods of detecting ligands and receptors. Radioimmunoassay is the most widely used method. This method employs a molecule which has been labeled with a radioactive isotope. By combining an antibody to the ligand (ligand is the compound to be determined) with a small amount of ligand which has been labeled with a radioactive isotope and separating ligand-bound-to-antibody from ligand which is unbound, the amount of ligand present in the original sample is determined from the amount of radioactive ligand remaining in the supernatant solution. U.S. Pat. No. 3,709,868 describes such a radioimmunoassay.

Several non-isotopic immunoassay methods have been proposed to eliminate the disadvantages associated with radioactive materials. For example, the radioactive label may be replaced with an enzyme (U.S. Pat. No. 3,654,090). By the addition of a ligand the distribution of the enzyme labeled component over the bound and free fraction is altered. The amount of soluble or insoluble enzyme labeled component can be determined by the specific enzyme activity, said amount being a measure of the ligand in the sample. In a preferred form of the invention the conjugated enzyme is detected by a color reaction, i.e. either a colored substrate or a colored end-product participates in the catalytic reaction which allows spectrophotmetric measurement.

Another enzyme immunoassay (U.S. Pat. No. 3,817,837) is marketed under the trademark EMIT. This is a homogeneous technique (the separation step is eliminated) such that antibody (or any other suitable receptor) when bound to the enzyme labeled ligand substantially inhibits enzymatic activity, providing for different catalytic efficiencies between the bound and unbound form of the enzyme.

The reaction of a substrate labeled ligand with an enzyme to produce a fluorescent product is described in U.S. Pat. No. 4,226,978. When antibody is bound to the substrate labeled ligand the enzyme is prevented from reacting with the substrate. The intensity of fluorescence is proportional to the amount of ligand present in the sample.

U.S. Pat. No. 4,166,105 and 4,169,137 describe antigen detecting reagents which are prepared by covalently linking fluorescent dye molecules to an appropriate antibody through a polymer possessing reactive functional groups.

Each of the foregoing prior art systems require the use of sophisticated instrumentation or complex procedures to measure the level of the biologically active substances. In contradistinction, the present invention provides immunoassay systems which may be used in the home relying on visual observation to determine the presence of biological substances. Furthermore, the present reagents are advantageous over prior art reagents in that they are highly sensitive permitting the detection of small amounts of ligands or receptors, more stable resulting in a longer shelf life, easier to prepare, and can be used for the detection of both high and low molecular weight substances.

SUMMARY OF THE INVENTION

The present invention relates to new polymers useful as reagents for the quantitative and qualitative measurement of ligands and receptors in physiological fluids. Ligand as used herein refers to a molecule, such as an antigen or hapten, which has a corresponding receptor such as an antibody. The ligands which can be detected in the present invention include those having a molecular weight in the range of from about 100 to about 20,000,000. Generally, such ligands include, for example, drugs, hormones, proteins, vitamins, viruses, bacteria, and enzymes. Receptors which can be detected include, for example, antibodies, specific binding proteins, and cell surface receptors.

The present polymers are those which absorb or emit photons in the visible or UV spectrum. Polymers of the present invention which absorb photons are derived from water soluble compounds having at least two functional groups selected from an amino group and a carboxyl group. Preferably, the compound has two amino groups or one amino group and one carboxyl group. Dyes are the most common example of the compounds useful in this invention.

A dye molecule typically contains chromogenic groups which absorb photons of specific wavelengths in the visible or the UV region. Auxochromic groups which are functional groups such as —SH, —OH, and —NR$_2$ where R is hydrogen or lower alkyl change the wavelength at which photons are absorbed. Usually, the presence of these groups results in absorption at a higher wavelength. Examples of such dyes include Congo Red, Trypan Blue and Lissamine Blue.

Polymers of this invention which emit photons are derived from water-soluble compounds which when illuminated radiate unpolarized light of a different wavelength due to the return of electrons, displaced by the exciting radiation, to a more stable position and which contain the same fuctional groups as the compounds mentioned above. The most common example of such compounds are fluorescent compounds.

The foregoing polymers can be linked to ligands to form a reagent suitable for the detection of the same ligand or a receptor which is the binding counterpart of the lignd bound to the polymer. In a similar manner the detection of a particular ligand or receptor to the ligand is effected by the use of a reagent containing a polymer of this invention bound to a receptor for the ligand. These novel reagents can be used in both homogeneous and hetergeneous immunoassay systems.

DETAILED DESCRIPTION OF THE INVENTION

The new polymers of this invention are divided into four classes. Each polymer must have a functional group for binding to ligand or receptor such as an amino, carboxyl or aldehyde group. The first class comprises a polymer having a plurality of photon absorbing or emitting monomers linked to each other through a linking group to form a polymer chain with a free functional group appearing at each end of the chain. If the functional groups of the monomer are amino groups only, the linking group is a difunctional aldehyde such as glutaraldehyde which forms part of the polymer. If the monomer has a combination of amino and carboxyl groups then, a peptidic link is formed with the use of, for example, carbodiimide.

The number of monomers is virtually unlimited ranging from a few monomers to well over 600 monomers. However, it is preferred to provide a chain with at least 40 monomers to achieve the desired sensitivity of the label. Also, an upper limit of 600 monomers is desirable where the formation of larger polymers takes too long. Most preferred is a polymer chain of between about 200 and 400 monomers.

The second class of polymers comprises a plurality non-photon absorbing or emitting monomers containing three or more functional groups linked to each other through a difunctional aldehyde such as glutaraldehyde, or a peptidic group, wherein each monomer of the polymer chain is bound to a photon absorbing or emitting molecule. Exemplary of the non-photon absorbing or emitting compounds are amino acids having two or more carboxylic or amino groups. Lysine, argine, amino-tyrosine and diamino benzoic acid are typical examples of amino acids having two amino groups. Glutamic acid and aspartic acid are amino acids with two carboxyl groups.

The non-photon absorbing or emitting compounds with one or more carboxyl groups and one or more amino groups can be polymerized in the presence of the difunctional aldehyde or carbodiimide to produce a polymer chain having the desired number of monomers described above with a free carboxyl group on each monomer. The free carboxyl groups can then be linked to a suitable photon absorbing or emitting molecule having at least one amino group such as Congo Red, Trypan Blue, Lissamine Blue, and amino fluorescein to produce a polymer label having a plurality of free carboxyl groups some of which act as binding sites for ligands or receptors.

The third class of polymers comprises repeating units of photon absorbind or emitting polymers and non-photon absorbing or emitting polymers. The polymers are linked to each other by a difunctional aldehyde which forms part of the polymer or carbodiimide. The difunctional aldehyde such as glutaraldehyde is used if each of the polymers has free terminal amino groups. Carbodiimide is used if one of the polymers has a free amino group and the other has a free carboxyl group. The weight ratio of the photon absorbing or emitting polymer to the non-photon absorbing or emitting polymer is generally between about 30:1 and 4:1.

Polymers of this class can be produced by first polymerizing a photon-absorbing or emitting compound such as Congo Red and then adding, for example, a diamino acid such as lysine and polymerizing the resulting product to provide a polymer having repeating units of polydye and a polymer of lysine.

The fourth class of polymers employs a molecule having a plurality of functional groups bound to any of the previously mentioned classes of polymers of this invention. Any molecule possessing multiple free amino groups, preferably between 10 and 100 free amino groups, and which does not substantially polymerize during the step of binding the photon absorbing or emitting polymers to the free amino groups may be used for this purpose. Exemplary of such molecules are synthetic or natural polypeptides having a large number of diamino acids (e.g. lysine and arginine) as, for example, polypeptidic polylysin. Particularly preferred is bovine serum albumin (BSA) which has 55 free amino groups.

The polymers of the first three classes of this invention may be linked to the free amino groups of the molecule by suitable linking groups such as a difunctional aldehyde and carbodiimide. This may be accomplished by first forming the photon absorbing or emitting polymer followed by linking the polymers to the molecule. Alternatively, the polymerization and linking steps may be performed simultaneously. The resulting polymers, having free carboxyl or amino groups may then be linked to ligands or receptors to form a reagent of this invention.

Preferably, each of the photon absorbing or emitting polymers linked to the molecule has between about 10 and 100 monomers. When BSA is employed as the molecule, it is preferable to use a weight ratio of BSA to th photon absorbing or emitting polymer between about 0.02:1 and 0.3:1, most preferably between about 0.05:1 and 0.1:1.

The weight ratio of ligand or receptor to the photon absorbing or emitting polymer bound to the molecule varies depending on the components selected. Generally the weight ratio is between about 1:1 and 10:1 for an antibody and between about 0.02:1 and 0.1:1 for a hapten having a molecular weight of about 500 daltons.

The four classes of polymers described above may all be used in a variety of immunoassay techniques including homogeneous assays wherein binding of the ligand or receptor to be detected to the reagent causes a change in the photometric properties of the label portion which can be observed by the naked eye or appropriate instrumentation such as a spectrophotometer or fluorometer. In one embodiment the presence of ligand or receptor is observed by the spontaneous formation of a colored precipitate corresponding to the color of the photon absorbing polymer.

The polymers of the present invention may be used as reagents in solid phase separation procedures as well as in a so-called "sandwich" procedure which is another example of a heterogeneous immunoassay system.

The following examples set forth preferred embodiments of the present invention and are not intended to limit the scope of the invention described in the claims annexed hereto.

EXAMPLE 1

Polymerization of Congo Red 10 mg of Congo Red were dissolved in 200 microliters of distilled water, and then diluted with 650 microliters of 0.03M sodium phosphate buffer (pH 7.4). 150 microliters of a 25% solution of glutaraldehyde were then added and the resulting solution was maintained at 10° C. for three days. The solution was dialysed against ordinary water and then against distilled water during a period of 24 hours.

An aliquot was taken of the final solution, which had been diluted during dialysis to 900 microliters, and was passed through a Sephadex G200 column (L=10 cm, $\phi=8$ mm) which showed that the polymerized dye was eluted in the exclusion volume of the column (MW >200,000).

EXAMPLE 2

Preparation of a Labeled Antigen with Polymerized Congo Red

An aliquot of 200 microliters of the solution produced in Example 1 was added to a solution of carbodiimide (Sigma ref. C. 2388), 5 mg. in 1 ml of phosphate buffer and 100 microliters of a solution of 100 micrograms of Human Placental Lactogen (HPL) hormone in distilled water.

The resulting mixture was combined with 200 microliters of the same phosphate buffer. After one day, 1 ml of this mixture was dialysed successively against ordinary and distilled water during 24 hours. The labeled antigen thus produced showed a slow rate of precipitation.

EXAMPLE 3

A Demonstration of the Immunoreactivity of the Labeled Antigen of Example 2

10 microliters of the labeled antigen of Example 2 were mixed with 400 microliters of HPL rabbit antiserum having a 1:2000 dilution during 1 hour and placed in a test tube. A reference tube of 10 microliters of the same labeled antigen diluted with 400 microliters of phosphate buffer was prepared.

500 microliters of a suspension containing approximately 12 mg of Sepharose 4B on which 25 micrograms of anti-rabbit immunoglobulin antibodies had been coupled by the standard Br/CN procedure were added to each of the tubes. The solid-phase was allowed to react for 30 minutes with the contents of each tube. The contents of both tubes were then washed three times with 2 ml of phosphate buffer. The solid-phase in the tube with the HPL antibody showed a pink color while the reference tube remained white.

Thus no reaction occured between the labeled antigen and the solid phase in the absence of the specific HPL antibody. In presence of antibody, the labeled antigen bound to the solid phase resulted in a color change.

EXAMPLE 4

Preparation of Congo Red Bound on a Glutaraldehyde-Lysine Polymer 100 microliters of a 25% solution of glutaraldehyde were added to 50 mg of lysine dissolved in 1.1 ml of distilled water. After 1 hour, the polymerization reaction was stopped by passing the reaction product through a column of Sephadex G 200 (L=10 cm; $\phi=8$ mm) and eluting with a phosphate buffer solution. The solution turned a dark yellow color confirming the formation of glutaraldehyde-lysine polymer having a molecular weight of between about 50,000 and 200,000 daltons. 5 ml of the colored eluate was recovered in 4 tubes.

5 mg of Congo Red in one ml of distilled water and 4 mg of carbodiimide in 400 microliters of water were added to one ml of the eluate in the second tube containing about 1 mg of the polymer. The reaction product spontaneously precipitated over a 24 hour period demonstrating the formation of the Congo Red bound glutaraldehyde-lysine polymer.

In order to limit a side reaction between the terminal amino groups and carboxylic groups of the glutaraldehyde-lysine polymer, the reaction can be halted by processes known in the art such as gel filtration, dialysis or by the addition of a suitable amount of glycine or alanine.

EXAMPLE 5

Preparation of a Copolymer having Alternating Polymers of Congo Red and Lysine 25 mg of Congo Red were dissolved in 2.3 ml of distilled water and added to 400 microliters of a 25% glutaraldehyde solution. After 5 days, the mixture was separated on a Sephadex G 200 column (L=15 cm; $\phi=18$ mm) and elution was effected with a phosphate buffer. Most of the resulting dye material was eluted with the exclusion volumn of the column. The eluant had a volume of 17.5 ml containing about 23 mg of polymerized Congo Red.

2.1 mg of lysin and 10 mg of carbodiimide were added to the Congo Red polymer and the reaction was permitted to take place over 24 hours. Then, the solution was dialysed against 200 ml of distilled water for 24 hours. The resulting solution containing a copolymer with alternating polymers of Congo Red and lysin was found to be fairly stable for more than four months.

1 ml of the solution was diluted with 1 ml of distilled water to which was added 100 microliters of a purified rabbit immunoglobulin (IgG) solution containing 1.2 mg of IgG. Purification of the rabbit IgG was conducted by the known process of selective precipitation using a saturated ammonium sulfate solution. 5 mg of carbodiimide were then added to the mixture and the reaction was allowed to proceed for 4 hours.

Subsequently, dialysis was performed on the resulting mixture against 200 ml of distilled water over 12 hours followed by the addition of 3 mg of lysine dissolved in 100 micorliters of water. The labeled antigen slowly precipitated from the solution over 24 hours.

EXAMPLE 6

Demonstration of the Immunoreactivity of the Labeled Antigen of Example 5

200 microliters of the labeled antigen solution was placed in each of 5 tubes and diluted with 300 microliters of phosphate buffer solution (pH 7.4). Tube 1 was maintained as a reference, and increasing amounts of anti-rabbit IgG sheep antiserum were added to the following tubes: 10 microliters in tube 2, 20 microliters in tube 3, 40 microliters in tube 4 and 80 microliters in tube 5.

Immediately after the addition of the antiserum, turbidity appeared in all the tubes except tube 1. The degree of turbidity was proportional to the antiserum concentration. However, as is well known in antigen-antibody reactions, there is an optimum antibody concentration which generates maximum precipitation. The optimum concentration in this example was 10 microliters of antiserum giving the best precipitation and the clearest supernatant.

The following test established that a competitive binding reaction occured between the labeled and unlabeled forms of the antigen for antibody binding sites.

200 microliters of the labeled antigen solution was diluted with 500 microliters of phosphate buffer and added to each of five tubes. Tube 1 was maintained as a reference while the remaining tubes received increasing amounts of rabbit serum according to the following scheme.
   Tube 2: 50 microliters of rabbit serum
   Tube 3: 100 microliters of rabbit serum
   Tube 4: 200 microliters of rabbit serum
   Tube 5: 350 microliters of rabbit serum
Then, 10 microliters of antirabbit IgG antiserum were added to each of the five tubes and the reaction was permitted to take place over two hours. A significant amount of precipitate was formed in tube 1 and a minor amount of tube 2. Tubes 3-5 showed no evidence of precipitation.

It is thus clear that a significant amount of antibody in tube 1 binds to the labeled antigen causing precipitation. On the other hand, the amount of free antigen in tubes 3-5 was sufficient to occupy substantially all of the antibody binding sites thereby limiting the formation of labeled antigen bound to antibody.

EXAMPLE 7

Formation of a Labeled Antibody 800 microliters of a solution containing the polymer of Examples 5 were mixed with 60 microliters of an antirabbit IgG purified antibody solution at a concentration of 15 mg/ml. 25 microliters of a 25% glutaraldehyde solution were then added. After 4 hours, the reaction was stopped by the addition of 10 mg of alanine in 250 microliters of water. The labeled antibody spontaneously precipitated in 6 hours.

EXAMPLE 8

Demonstration of the Immunoreactivity of the Labeled Antibody of Example 7

Two tubes were prepared each containing 20 microliters of the solution containing the labeled antibody as shown in Example 7 diluted with 500 microliters of phosphate buffer. Tube 1 was maintained as a reference while 10 microliters of a 1:50 dilution of rabbit serum were added to tube 2. Turbidity appeared in tube 2 after 5 minutes and heavy precipitation occurred after one hour. Tube 1 showed very slight precipitation during the same time period. The labeled antibody thus binds to the free antigen in the sample to produce an insoluble compound which spontaneously precipitates from the solution.

EXAMPLE 9

Double Antibody System Using the Labeled Antibody of Example 7

300 microliters of the solution containing the labeled antibody of Example 7 (containing 210 micrograms of antirabbit antibodies) are mixed with 10 microliters (120 micrograms) of rabbit anti HCG antiserum (anti human chorionic gonadotrophin hormone).

20 microliters of this mixture diluted with 500 microliters of phosphate buffer were added to each of two tubes. Tube 1 was maintained as a reference while 50 microliters of a solution containing 2000 IU/ml of HCG were added to tube 2. Tube 2 showed immediate turbidity establishing that HCG was bound to its antibody in the double antibody complex.

The same assay was performed on a urine sample. 40 microliters of the above-described double antibody solution were mixed with 400 microliters of phosphate buffer (pH 7.4) and the resulting solution was added to 1 ml of male urine. The mixture was then added to each of two tubes the second of which also received 10 microliters of a solution containing 10 IU of HCG. Precipitation was observed in tube 2 after two hours and no precipitation was observed in Tube 1.

EXAMPLE 10

A Competitive Binding Assay Using a Copolymer of Alternating Polymers of Congo Red and Lysine 25 mg of Congo Red were dissolved in 2.3 ml of distilled water and added to 400 microliters of a 25% glutaraldehyde solution. 10% by weight of lysine based on the weight of polymerized Congo Red was added to the solution. 380 microliters of a solution containing 500 micrograms of the resulting product was added to 80 microliters of glutaraldehyde. After 24 hours, the resulting copolymer was dialysed against ordinary and distilled water followed by the addition of 200 microliters of a solution containing 1000 IU of HCG. The reaction was stopped after 15 hours by the addition of 5 mg of glycine. Phosphate buffer (pH 7.4) was then added to provide a 1 ml. solution.

A double antibody solid phase was prepared by saturating Sepharose 4B bound to a second antibody with anti HCG antibody followed by washing to produce a Sepharose 4B suspension. Two tubes were prepared each containing 100 microliters of the Sepharose suspension prepared above (containing about 10 micrograms of anti HCG antibody) mixed with 100 microliters of phosphate buffer, 50 microliters of a solution containing 0.5 mg of bovine serum albumin, and 500 microliters of water. Tube 2 was additionally provided with 200 microliters of a solution containing 100 IU of HCG.

After 10 minutes, 50 microliters of the labeled antigen were added to each of the two tubes. The reaction was allowed to proceed for two hours. At the conclusion of the reaction, the tube 1 solid phase was deeply colored while the tube 2 solid phase had a much lighter color establishing that HCG binds to the double antibody Sepharose.

EXAMPLE 11

Solid Phase Assay Using The Labeled Antigen of Example 10

The labeled antigen described in Example 10 was employed in a heterogeneous solid phase immunoassay in the following manner.

600 microliters of a solution containing 1.38 mg of glutaraldehyde-lysine polymer prepared in accordance with Example 4 were mixed with 100 microliters of a solution containing 1.2 mg of purified antirabbit immunoglobulins and 4 mg of carbodiimide. The reaction was allowed to proceed for 10 hours followed by dialysis against distilled water for 24 hours.

250 microliters of rabbit anti HCG serum were added to the mixture resulting in the formation of a heavy precipitate. The precipitate was washed 5 times with 3 ml of distilled water and a final suspension was prepared having a volume of 2.5 ml.

An assay was then conducted using the solid phase described above with the labeled antigen following the same procedure described in Example 10.

EXAMPLE 12

Preparation of a Polymer of Congo Red on BSA and Formation of Labeled Antigen 9 mg of Congo Red dissolved in 0.9 ml of water, 10 microliters of a solution containing 0.4 mg of bovine serum albumin (BSA) and 150 microliters of a 25% glutaraldehyde solution were mixed together.

After 3 days, the resulting solution was dialysed against ordinary and distilled water. Distilled water was added to provide a final volume of 2.5 ml. 28 microliters of this solution were mixed with 50 microliters of a solution containing 250 IU of HCG (83 micrograms) and 200 microliters of water. After 10 hours, 4 mg of glycine were added, and 2 hours later, 100 microliters of phosphate buffer (pH 7.4).

EXAMPLE 13

Assay Using the Labeled Antigen of Example 12 In a Competitive Reaction Procedure 25 microliters of the solid phase suspension of Example 11 and containing 5 micrograms of anti HCG antibody were diluted with 100 microliters of phosphate buffer, 50 microliters of a solution containing BSA and 500 microliters of water and the mixture was added to each of three tubes. Tube 2 was provided with 5 microliters of a solution containing 25 IU of HCG while tube 3 received 20 microliters containing 100 IU of HCG. The reactions were allowed to proceed for 30 minutes followed by the addition of 40 microliters of the labeled antigen solution of Example 12 into each tube.

After three hours, the solid phase in tube 1 showed the most color with less color in tube 2 and the least color in tube 3. The reduction in color in tubes 2 and 3 proves that a portion of the labeled antigen competes with the free antigen of the test sample.

EXAMPLE 14

Preparation of a Polymer of Trypan Blue and BSA and Binding Said Polymer with Antibody 13.2 mg of Trypan Blue in 1 ml of water were mixed with 350 microliters of a solution containing 1.3 mg of BSA and 200 microliters of a 25% solution of glutaraldehyde. After 3 days, the resulting product was dialysed twice against distilled water for 24 hours to produce a final solution having a volume of 2.8 ml.

100 microliters of this solution was added to 350 microliters of a solution containing 4 mg of purified antirabbit immuloglobulin antibodies. The reaction took place for 24 hours followed by the addition of 100 microliters of a solution containing 2 mg of lysine. The final solution was diluted to 5 ml with distilled water.

The formation of the labeled antibody was established in the following manner. Seven tubes were prepared each containing 100 microliters of the labeled antibody, 100 microliters of phosphate buffer (pH 7.4) and 1 ml of water. Rabbit serum was added to tubes 1-6 as follows:

Tube 1: 5 microliters of rabbit serum
Tube 2: 2.5 microliters of rabbit serum
Tube 3: 1.2 microliters of rabbit serum
Tube 4: 0.40 microliters of rabbit serum
Tube 5: 0.20 microliters of rabbit serum
Tube 6: 0.10 microliters of rabbit serum Tube 7 was maintained as a reference receiving no rabbit serum. Tube 7 showed a deep violet color while tube 6 showed a slight change from violet to blue and the remaining tubes showed a more complete change to blue directly proportional to the quantity of rabbit serum in the tube. Thus, the labeled antibody binds to the antigen producing a color change.

EXAMPLE 15

Quantitative Measurement in an Assay Using the Labeled Antibody of Example 14

50 microliters of the Trypan Blue-BSA polymer described in Example 14 were mixed with 50 micrograms of lysine. Lysine was added to block the reactive CHO groups of the polymer. After 6 hours, the product was dialysed against distilled water for 24 hours after which 1 ml of a solution containing 1.0 mg of antirabbit antibodies and 5 microliters of a 25 % glutaraldehyde solution were added. The reaction proceeded for 12 hours followed by the addition of 100 microliters of a solution containing 2 mg of lysine. The final solution had a volume of 2.5 ml.

Two tubes were prepared each containing 100 microliters of the labeled antibody solution, 100 microliters of phosphate buffer (pH 7.4) and 1 ml of water. 5 microliters of rabbit serum were added to tube 1 and an immediate color change was observed.

The contents of both tubes were diluted to provide a solution containing 75 microliters in 1 ml of water. The tubes were placed in a spectrophotometer and a measurement was made at 195 nm in 10 mm standard cuvettes. The optical density absorbance for tube 2 was 0.900 and 1.590 for tube 1.

EXAMPLE 16

An Assay for the Detection of Theophylline Using the Trypan Blue-BSA Polymer of Example 14

100 microliters of the Trypan Blue-BSA polymer prepared in accordance with Example 14 are added to 200 microliters of a solution containing 3 mg of theophylline. The reaction proceeds for 6 hours followed by dialysis twice against distilled water for 12 hours. The resulting labeled antigen is mixed with 200 microliters of phosphate buffer. The final volume is 500 microliters.

Two tubes are prepared with 50 microliters of normal human serum, 100 microliters of phosphate buffer (pH 7.4), and 20 microliters of the labeled antigen. 20 microliters of a solution containing 5 micrograms of theophylline are added to tube 1. Tube 2 is maintained as a reference. 100 microliters of a solution containing a 1:500 dilution of antitheophylline antiserum are added to each of the tubes. The color of the resulting solution in tube 2 changes from violet to blue depending on the concentration of theophylline in the sample. A competitive binding reaction occurs when the labeled antigen (theophylline) competes with the free antigen for the limited number of antitheophylline binding sites. The larger the amount of free theophylline present in the sample, the smaller the amount of antitheophylline available to bind to the labeled antigen and the smaller the color change. The color shift from violet to blue is thus inversely proportional to the amount of theophylline in the sample.

EXAMPLE 17

Polymerization of Congo Red in the Presence of an Antigen and Assay Using said Polymer 1.7 ml of a solution containing 1.2 mg of purified antirabbit immunoglobulins were added to 300 microliters of a solution containing 3 mg of Congo Red and 30 microliters of a 25% glutaraldehyde solution. After 12 hours, 4 mg of glycine were added and after 2 more hours, 1 ml of phosphate buffer giving a final volume of 3 ml.

An assay was conducted by first preparing a solid phase as described in Example 11. More specifically, 600 microliters of a solution containing 1.38 mg of glutaraldehyde-lysine polymer were added to 100 microliters of a solution containing 1.2 mg of purified antirabbit immunoglobulins and 4 mg of carbodiimide. 200 microliters of this mixture were added to 50 microliters of rabbit serum and the precipitate was washed three times with 2 ml of water. A final suspension was made in 1 ml of phosphate buffer.

Three tubes were prepared each containing 10 microliters of the labeled antibody described above, 1 ml of water, and 50 microliters of a solution containing 2 mg of BSA. Tubes 2 and 3 were also provided with 2 microliters and 10 microliters of rabbit serum, respectively. Tube 1 was maintained as a reference.

The reaction proceeded for one hour followed by the addition of 50 microliters of the above-described solid phase suspension. After 4 hours, tube 1 showed the most color and tube 3 the least color. Thus, the greater the amount of antigen (rabbitt serum) the greater the amount of color change which corresponds to the degree of binding between the labeled antibody and free antigen.

What is claimed is:

1. A reagent for the detection in biological fluids of one member of a binding pair selected from the group consisting of a ligand and a receptor in a buffered medium comprising a water-soluble polymer consisting essentially of between 40 and 600 chromophoric or fluorescent group containing monomers, a plurality of said monomers being bound to either of said members through a functional group.

2. The reagent of claim 1 wherein said monomers have at least two free amino groups and are linked to each other through a difunctional aldehyde.

3. The reagent of claim 2 wherein said difunctional aldehyde is glutaraldehyde.

4. The reagent of claim 2 wherein said monomer is lysine and said difunctional aldehyde is glutaraldehyde.

5. The reagent of claim 1 wherein said monomers have at least one free amino group and one free carboxyl group and are linked to each other through a peptidic group.

6. The reagent of claim 1 wherein the number of monomers is between about 200 and 400.

7. The reagent of claim 1 wherein said chromophoric group containing monomer is a dye compound.

8. The reagent of claim 7 wherein said dye compound is selected from the group consisting of Congo Red, Trypan Blue and Lissamine Blue.

9. The reagent of claim 1 wherein said fluorescent group containing monomer is amino fluorescein.

10. The reagent of claim 1 wherein said functional group is selected from the froup consisting of an amino group, a carboxyl group and an aldehyde group.

11. The reagent of claim 1 wherein said ligand is selected from the group consisting of drugs, hormones, proteins, vitamins, viruses, bacteria and enzymes.

12. The reagent of claim 1 wherein said receptor is selected from the group consisting of antibodies, specific binding proteins and cell surface receptors.

13. A reagent for the detection in biological fluids of one member of a binding pair selected from the group consisting of a ligand and a receptor in a buffered medium comprising a water-soluble co-polymer consisting essentially of alternating first and second polymers in a weight ratio of between 30:1 and 4:1, said first polymer having between 40 and 600 chromophoric or fluorescent group containing monomers, said second polymer having a plurality of non-chromophoric or non-fluorescent group containing monomers and a plurality of said monomers being bound to either of said members through a functional group.

14. The reagent of claim 13 wherein said first and second polymers have three terminal groups selected from the group consisting of amino, carboxyl and aldehyde groups and are linked to each other through a difunctional aldehyde or a peptidic group.

15. The reagent of claim 14 wherein said difunctional aldehyde is glutaraldehyde.

16. The reagent of claim 14 wherein one of said first and second polymers has a terminal amino group and the other has a terminal carboxyl group and said polymers are linked to each other through a peptidic group.

17. The reagent of claim 13 wherein said chromophoric of fluorescent group containing monomers are linked to each other through a functional group selected from the group consisting of a difunctional aldehyde and a peptidic group.

18. The reagent of claim 17 wherein said difunctional aldehyde is glutaraldehyde.

19. The reagent of claim 13 wherein said non-chromophoric or non-fluorescent group containing monomers are linked to each other through a functional group selected from the group consisting of a difunctional aldehyde and a peptidic group.

20. The reagent of claim 19 wherein said difunctional aldehyde is glutaraldehyde.

21. The reagent of claim 13 wherein said chromophoric group containing monomer is a dye compound.

22. The reagent of claim 21 wherein said dye compound is selected from the group consisting of Congo Red, Trypan Blue and Lissamine Blue.

23. The reagent of claim 13 wherein said fluorescent group containing monomer is amino fluorescein.

24. The reagent of claim 19 wherein said non-chromophoric or non-fluorescent group containing monomers are amino acids selected from lysin, argininie, amino tyrosine, diamino benzoic acid, glutamic acid and aspartic acid.

25. The reagent of claim 24 wherein said amino acid lysine and said difunctional aldehyde is glutaraldehyde.

26. The reagent of claim 13 wherein said functional group is selected from the group consisting of an amino group, a carboxyl group and an aldehyde group.

27. The reagent of claim 13 wherein said ligand is selected from the group consisting of drugs, hormones, proteins, vitamins, viruses, bacteria and enzymes.

28. The reagent of claim 13 wherein said receptor is selected from the group consisting of antibodies, specific binding proteins and cell surface receptors.

29. A reagent for the detection in biological fluids of one member of a binding pair selected from the group consisting of a ligand and a receptor comprising a water soluble polymer consisting essentially of a compound bound to between 10 and 100 first polymers through an amino group, said compound having between 10 and 100 free amino groups and said compound being one which does not substantially polymerize during binding to said first polymers, said first polymers selected from the group consisting of:
- (a) a water-soluble polymer consisting essentially of between 40 and 600 chromophoric or fluorescent group containing monomers; and
- (b) a water-soluble copolymer consisting essentially of alternating second and third polymers in a weight ratio of between 30:1 to 4:1, said second polymer having between 40 and 600 chromophoric or fluorescent group containing monomers, said third polymer having a plurality of non-chromophoric or non-fluorescent group containing monomers, and either of said members being bound to a plurality of said first polymers through a functional group.

30. The reagent of claim 29 wherein said functional group is selected from the group consisting of an amino group, a carboxyl group and an aldehyde group.

31. The reagent of claim 29 wherein said compound is selected from the group consisting of polypeptides and bovine serum albumin.

32. The reagent of claim 31 wherein said polypeptide is polypeptidic polylysine.

33. The reagent of claim 29 wherein said compound is linked to said first polymers through a linking group selected from the group consisting of a difunctional aldehyde and a peptidic group.

34. The reagent of claim 29 wherein said difunctional aldehyde is glutaraldehyde.

35. The reagent of claim 34 wherein said compound is bovine serum albumin and the weight ratio of said compound to said first polymers is between about 0.02:1 and 0.3:1.

36. The reagent of claim 35 wherein said weight ratio is between about 0.05:1 and 0.1:1.

37. The reagent of claim 29 wherein an antibody is bound to said first polymers through a functional group and the weight ratio of said antibody to said first polymer is between about 1:1 and 10:1.

38. The reagent of claim 29 wherein said ligand is selected from the group consisting of drugs, hormones, proteins, vitamins, viruses, bacteria and enzymes.

39. The reagent of claim 29 wherin said receptor is selected from the group consisting of antibodies, specific binding proteins and cell surface receptors.

40. In an assay method for determining the presence in a biological fluid of one member of a binding pair selected from the group consisting of a ligand and a receptor in an aqueous medium which comprises combining at least one reagent, said biological fluid suspected of containing said member, and a buffer under conditions which permit a ligand-receptor binding reaction and determining the amount of the absorbance or emission of photons or the formation of a precipitate in said medium, the improvement comprising employing a reagent selected from the group consisting of:
- (a) a water-soluble polymer consisting essentially of between 40 and 600 chromophoric or fluorescent group containing monomers, a plurality of said monomers being bound to either of said members through a functional group;
- (b) a water-soluble copolymer consisting essentiallyof alternating first and second polymers in a weight ratio of between 30:1 to 4:1, said first polymer having between 40 and 600 chromophoric or fluorescent group containing monomers, said second polymer having a plurality of non-chromophoric or non-fluorescent group containing monomers, and a plurality of said monomers being bound to either of said members through a functional group; and
- (c) a water soluble polymer consisting essentially of a compound bound to between 10 and 100 first polymers through an amino group, said compound having between 10 and 100 free amino groups and said compound being one which does not substantially polymerize during binding to said first polymers, said first polymers selected from the group consisting of:
  - (1) a water-soluble polymer consisting essentially of between 40 and 600 non-chromophoric or fluorescent group containing monomers; and
  - (2) a water-soluble copolymer consisting essentially of alternating second and third polymers in a weight ratio between 30:1 to 4:1, said second polymer having between 40 and 600 chromophoric or fluorescent group containing monomers, said third polymer having a plurality of non-chromophoric or non-fluorescent containing monomers, and either of said members being bound to a plurality of said first polymers through a functional group.

41. The assay method of claim 40 wherein said chromophoric group is a dye compound.

42. The assay method of claim 41 wherein said dye compound is selected from the group consisting of Congo Red, Trypan Blue and Lissamine Blue.

43. The assay method of claim 40 wherein said ligand is selected from the group consisting of drugs, hormones, proteins, vitamins, viruses, bacteria and enzymes.

44. The assay method of claim 40 wherein said non-chromophoric or non-fluorescent group containing monomers are amino acids selected from the group consisting of lysine, arginine, amino tyrosine, diamino benzoic acid, glutamic acid and aspartic acid.

45. The assay method of claim 40 for the detection in a biological fluid of a ligand wherein said reagent includes an analog of said ligand, said medium further containing a limited amount of an antibody to said ligand, said method further comprising:
- (a) permitting said reagnet and said ligand to undergo a competitive binding reaction with said antibody;
- (b) removing said antibody bound to said ligand and said antibody bound to said reagent from said medium;
- (c) determining the amount of absorbance or emission of photons of said medium containing unreacted reagent; and
- (d) comparing said amount with the amount of absorbance or emission of photons of a standard solution containing a known amount of ligand.

46. The assay method of claim 45 wherein the step of removing said antibody bound to said ligand and said antibody bound to said reagent further comprises:
- (a) adding a solid phase support bound to a second antibody to said medium, said second antibody capable of binding to said antibody bound to said ligand and said antibody bound to said reagent;
- (b) allowing said antibody bound to said ligand and said antibody bound to said reagent to bind to said solid phase; and
- (c) separating said solid phase bound to said antibody bound to said ligand and said antibody bound to said reagent from said medium.

47. The assay method of claim 46 wherein the amount of absorbance of photons is determined by observing a color change on said solid phase.

48. The assay method of claim 40 for the detection in a biological fluid of a ligand having at least two binding sites for an antibody to said ligand wherein said reagent includes said antibody for said ligand, said medium further containing a solid phase support bound to said antibody, said method further comprising:
(a) combining said ligand and said reagent wherein said ligand binds to said reagent;
(b) reacting said bound ligand with said solid phase wherein said bound ligand binds to said solid phase;
(c) determining the amount of absorbance or emission of photons of said medium containing unreacted reagent; and
(d) comparing said amount with the amount of absorbance or emission of photons for a standard solution containing a known amount of ligand.

49. The assay method of claim 48 wherein the amount of absorbance of photons is determined by observing a color change on said solid phase.

50. The assay method of claim 40 for the detection in a biological fluid of a ligand wherein said reagent includes an antibody for said ligand, said method further comprising:
(a) reacting said reagent and said ligand wherein said ligand binds to said reagent;
(b) determining the amount of the absorbance or emission of photons of said medium; and
(c) comparing said amount with the amount of absorbance or emission of photons of a standard solution containing a known amount of liquid.

51. The assay method of claim 50 wherein the amount of absorbance of photons is determined by observing a color change in said medium.

52. The assay method of claim 40 for the detection in a biological fluid of a ligand wherein said reagent (c) includes an analog of said ligand, said medium further containing antibody to said ligand, said method further comprising:
(a) permitting said reagent and said ligand to undergo a competitive binding reaction with said antibody;
(b) determining the amount of the absorbance or emission of photons of said medium; and
(c) comparing said amount with the amount of absorbance or emission of photons of a standard solution containing a known amount of said ligand.

53. The assay method of claim 52 wherein the amount of absorbance of photons is determined by observing a color change in said medium.

54. The assay method of claim 40 for the detection in a biological fluid of a ligand wherein said reagent includes an antibody for said ligand, said method further comprising:
(a) reacting said ligand and said reagent wherein said ligand binds to said reagent to form a precipitate;
(b) removing said precipitate from said medium;
(c) measuring the amount of absorbance or emission of photons of said medium containing unreacted reagent; and
(d) comparing said amount with the amount of absorbance or emission of photons of a standard solution containing a known amount of said ligand.

55. The assay method of claim 40 for the detection in a biological fluid of a first antibody wherein said reagent includes a second antibody which is capable of binding to said first antibody, said method further comprising:
(a) combining said reagent and said first antibody to thereby form a precipitate;
(b) removing said precipitate from said medium;
(c) determining the amount of absorbance or emission of photons of said medium containing unreacted reagent; and
(d) comparing said amount with the amount of absorbance or emission of photons of a standard solution containing a known amount of said first antibody.

56. The assay method of claim 40 for the detection in a biological fluid of a first antibody wherein said reagent (c) includes a second antibody which is capable of binding to first antibody, said method further comprising:
(a) combining said reagent and said first antibody;
(b) determining the amount of absorbance or emission of photons of said medium; and
(c) comparing said amount with the amount of absorbance or emission of photons of a standard solution containing a known amount of said first antibody.

57. The assay method of claim 40 wherein the amount of absorbance of photons is determined by observing a color change in said medium.

* * * * *

UNITED STATES PATENT AND TRADEMARK OFFICE
CERTIFICATE OF CORRECTION

PATENT NO. : 4,452,886
DATED : June 5, 1984
INVENTOR(S) : Robert P. Henry

It is certified that error appears in the above-identified patent and that said Letters Patent is hereby corrected as shown below:

Col. 2, line 63, change "lignd" to --ligand--;
         line 68, change "hetergeneous" to --heterogeneous--.
Col. 3, line 54, change "absorbind" to --absorbing--.
Col. 4, line 14, change "polylysin" to --polylysine--;
         line 30, change "th" to --the--.
Col. 6, line 43, change "micorliters" to --microliters--.
Col. 7, line 15, change "of" (first occurrence) to --in--;
         line 27, change "Examples" to --Example--;
         line 29, change "glutaraled-" to --glutaralde- --.
Col. 12, line 47, change "lysin" to --lysine--;
         line 50, after "acid" insert --is--.
Col. 13, line 30, change "34" to --31--.
Col. 14, line 45, change "reagnet" to --reagent--.
Col. 15, line 19, change "for" to --of--;
         line 35, change "liquid" to --ligand--.

Signed and Sealed this

Twentieth Day of November 1984

[SEAL]

Attest:

GERALD J. MOSSINGHOFF

Attesting Officer

Commissioner of Patents and Trademarks